United States Patent [19]

Irikura et al.

[11] Patent Number: 4,914,104
[45] Date of Patent: Apr. 3, 1990

[54] IMIDAZO [1,5-A]PYRIMIDINE DERIVATIVES AND PROCESS FOR THEIR PREPARATION

[75] Inventors: Tsutomu Irikura, Tokyo; Seigo Suzue, Kuki; Satoshi Murayama, Tochigi; Susumu Kinoshita, Okaya; Hiroaki Uchida, Tokyo; Hirotaka Shinoda, Kawaguchi, all of Japan

[73] Assignee: Kyorin Pharmaceutical Co., Ltd., Tokyo, Japan

[21] Appl. No.: 294,905

[22] Filed: Jan. 4, 1989

Related U.S. Application Data

[63] Continuation of Ser. No. 918,648, Oct. 14, 1986, abandoned, which is a continuation of Ser. No. 758,445, Jul. 24, 1985, abandoned.

[30] Foreign Application Priority Data

Aug. 7, 1984 [JP] Japan .................................. 59-165468

[51] Int. Cl.$^4$ .................. A61K 31/505; C07D 487/04
[52] U.S. Cl. ..................................... 514/258; 544/281; 544/310
[58] Field of Search .......................... 544/281; 514/258

[56] References Cited

U.S. PATENT DOCUMENTS 4,178,449 12/1979 Dusza et al. ........................ 544/281
4,236,005 11/1980 Dusza et al. ........................ 544/281

FOREIGN PATENT DOCUMENTS 0134928 3/1985 European Pat. Off. ............ 544/281
2160020 6/1973 Fed. Rep. of Germany ...... 544/281

OTHER PUBLICATIONS

*Medicinal Chemistry* (3rd Ed.) Alfred Burger, Editor, p. 603 (1970).

*Primary Examiner*—Anton H. Sutto
*Assistant Examiner*—E. Bernhardt
*Attorney, Agent, or Firm*—Oblon, Spivak, McClelland, Maier & Neustadt

[57] ABSTRACT

This invention relates to a novel imidazo[1,5-a]pyrimidine derivatives and process for their preparation.

Moreover, it relates to novel imidazo[1,5-a]pyrimidine derivatives and salts thereof having antifungal activities, and process for their preparation.

2 Claims, No Drawings

IMIDAZO [1,5-A]PYRIMIDINE DERIVATIVES AND PROCESS FOR THEIR PREPARATION

This application is a continuation of application Ser. No. 06/918,648, filed on Oct. 14, 1986, now abandoned, which is a continuation of application Ser. No. 758,445, filed 7/24/85 now abandoned.

DETAILED DESCRIPTION OF THE INVENTION

This invention relates to a new class of compounds of the imidazo [1,5-a]pyrimidine series. It relates also to the synthesis of such substances. It is concerned further with salts of these compounds such as hydrochloride, sulfate, acetate, tartrate and methanesulfonate.

These new compound of the invention have the general formula (I),

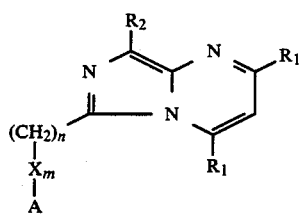

wherein $R_1$ is a halogen atom, $R_2$ is a hydrogen atom or a halogen atom, X is a sulfur atom, a sulfinyl group, a sulfonyl group or an oxygen atom, m and n are each independently 0 or 1, A is a phenyl group which may be substituted, a cycloalkyl group or a aromatic heterocyclic group which may be substituted (but when m is 0 and A is a phenyl group which may be substituted or a cycloalkyl group, $R_2$ is not a hydrogen atom).

It has been found that these compounds possess valuable pharmacological properties. For instance they produce antifungal effects and may be used for therapeutic properties.

Recently, fungal diseases are on the increase internationally because of frequent use of broad spectrum antibiotics, steroid hormones and immunosuppressive agents et cetera. However, useful antifungal agents in therapy of fungal diseases are limited. At present, it might almost be said that the only drugs for fungal diseases are polyenmacrolide and imidazole derivatives. It has been hoped that more useful antifungal agents for treatment of fungal disease could be developed. Therefore, we have studied earnestly to develop compounds having useful activity, especially potent antifungal activity. As a result of out study, we have found novel imidazo[1,5-a]pyrimidine derivatives having different structures and high potency against various organisms as compared with known antifungal agents. The compounds of the present invention and their salts are new compounds which have not been disclosed in any references. The present compounds may be used not only as a medicines for humans, but also as drugs for animals, fishes and shellfish, and as antiseptics for food in the various forms.

As suitable salts of the compounds represented by the formula (I), there may be mentioned salts derived from inorganic acid, such as, for example, hydrochloric acid, sulfuric acid, or salts derived from organic acids, such as, for example, acetic acid, tartaric acid, methanesulfonic acid, or the like.

These new compounds can be prepared by the method mentioned below.

The N-acylaminomethylpyrimidine compounds represented by the formula (II) were converted to the imidazo[1,5-a]pyrimidine compounds having the formula (III) by the condensing agents such as phosphorous halide and phosphoryl halide, for example phosphorous trichloride, phosphorous pentachloride, phosphorous tribromide, phosphoryl chloride, and thionyl chloride.

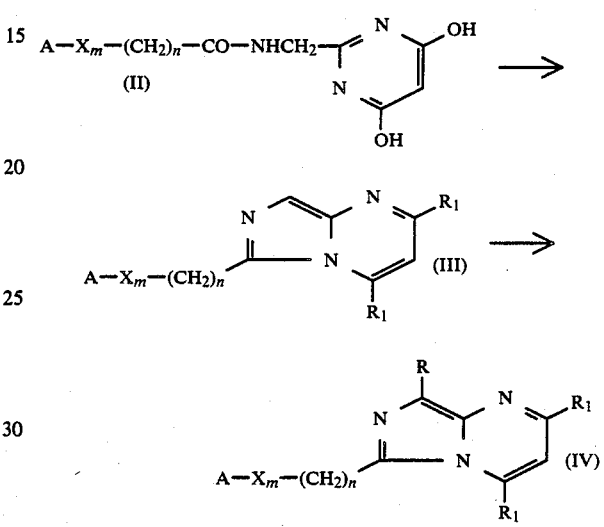

wherein A, X, m, n and $R_1$ have the previously defined meanings, R is a halogen atom.

If necessary, the compound represented by the formula (III) can be converted to the compound represented by the formula (IV) by treatment with a halogenation agent such as N-bromosuccinimide, N-chlorosuccinimide. The compound having a thio group in the formula (III) or (IV) can also be oxidized; the thio group to sulfinyl or sulfonyl group by the usual manner.

N-acylaminomethylpyrimidine compounds having the formula (II), the starting materials in the reaction discussed above, are also novel compounds and can be prepared by the following methods.

The method for preparing these compounds involves (a) reaction of glycine ethyl ester hydrochloride with various acid chlorides to give N-acyl derivatives of glycine ethyl ester and (b) treatment of these N-acyl derivatives with malonamide to give the desired compounds (II). These reactions are summarized in the following scheme.

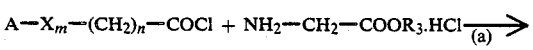

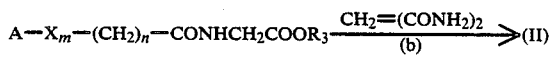

wherein A, X, m and n have the previously defined meanings, $R_3$ is a lower alkyl group.

PREPARATION OF INTERMEDIATE COMPOUNDS

REFERENCE 1

Preparation of 2-[N-(2-thenoyl)aminomethyl]-4,6-dihydroxypyrimidine (i) N-(2-thenoyl)glycine ethyl ester To a solution of glycine ethyl ester hydrochloride (22 g) and potassium carbonate (86 g) in water (600 ml) was added a mixture of benzene (600 ml) and ether (400 ml) and stirred at room temperature. 2-Thenoyl chloride (25 g) in benzene (100 ml) was added during a period of about 30 minutes under stirring and then the mixture was stirred for 2 hours at room temperature. The organic layer was separated and after dried over anhydrous sodium sulfate, concentrated under reduced pressure to give colorless crystals, which were recrystallized from ethanol to obtain the objective compound (23 g), mp 82°–83° C.

(ii) 2-[N-(2-thenoyl)aminomethyl]-4,6-dihydroxypyrimidine.

To a solution of sodium (1.4 g) in ethanol (120 ml) was added malonamide (3.8 g) and the mixture was heated at 60° C. for an hour under stirring. Then after added N-(2-thenoyl)glycine ethyl ester (8 g), the mixture was refluxed for 6 hours. The mixture was concentrated to give the residue which was diluted with water. The aqueous mixture was neutralized by adding acetic acid to deposit a crystalline product which was collected by filtration and recrystallized from dimethylformamide (DMF) to give the objective product (2.8 g) as colorless crystals, mp 270°–275° C. (decompd.).

Analysis (%) for $C_{10}H_9N_3O_3S$, Calcd. (Found): C, 47.80 (47.83); H, 3.61 (3.67); N, 16.72 (16.96).

Other compounds prepared by the same manner as this example are as follows.

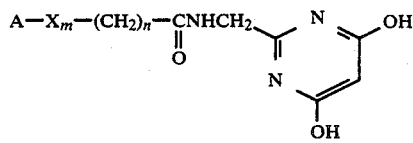

| Reference example | A | X | m | n | formula | mp (°C.) |
|---|---|---|---|---|---|---|
| 2 | (phenyl-isoxazole) | — | 0 | 0 | $C_{15}H_{12}N_4O_4$ | 220–225 (decompd.) |
| 3 | (furan) | — | 0 | 0 | $C_{10}H_9N_3O_4$ | 285–290 (decompd.) |
| 4 | (thiophene) | — | 0 | 1 | $C_{11}H_{11}N_3O_3S$ | 275–285 (decompd.) |
| 5 | (thiophene) | — | 0 | 0 | $C_{10}H_9N_3O_3S$ | >300 |
| 6 | (Br-thiophene) | — | 0 | 0 | $C_{10}H_8N_3O_3BrS$ | 250–255 (decompd.) |
| 7 | (Cl-thiophene) | — | 0 | 0 | $C_{10}H_8N_3O_3ClS$ | >300 |
| 8 | (CH3-thiophene) | — | 0 | 0 | $C_{11}H_{11}N_3O_3S$ | 269–276 (decompd.) |
| 9 | (pyridine) | — | 0 | 0 | $C_{11}H_{10}N_4O_3$ | 255–260 (decompd.) |

-continued

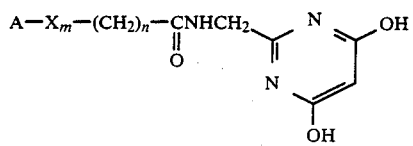

| Reference example | A | X | m | n | formula | mp (°C.) |
|---|---|---|---|---|---|---|
| 10 | (benzothiophene-Cl) | — | 0 | 0 | $C_{14}H_{10}N_3O_3SCl$ | 185–195 (decompd.) |

EXAMPLE 1

2,4-dichloro-6-(2-thienyl)imidazo[1,5-a]pyrimidine

A mixture of 2-[N-(2-thenoyl)aminomethyl]-4,6-dihydroxypyrimidine (1.3 g) and phosphoryl chloride (10 ml) was heated to reflux for 3 hours. The excess phosphoryl chloride was removed by distillation under reduced pressure. To the resulting residue was added an aqueous sodium carbonate solution and the mixture was extracted with chloroform. The chloroform layer was washed with water, dried over anhydrous sodium sulfate and concentrated. The residue was purified by alumina column chromatography, eluting with benzene and then by recrystallization to give the objective compound (0.56 g) as yellow plates, mp 152°–153° C.

Analysis (%) for $C_{10}H_5N_3SCl_2$, Calcd. (Found): C, 44.46 (44.32); H, 1.87 (1.67); N, 15.56 (15.56).

Other compounds prepared by the same manner as this example are as follows.

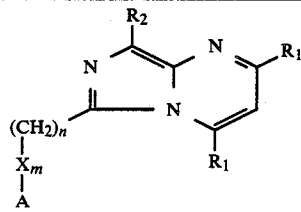

| Example | $R_1$ | $R_2$ | A | X | m | n | Formula | mp (°C.) | Analysis Calcd. (%) Found C | H | N |
|---|---|---|---|---|---|---|---|---|---|---|---|
| 2 | Cl | H | (phenyl-isoxazole) | — | 0 | 0 | $C_{15}H_8N_4OCl_2$ | 149–150 | 54.40 / 54.37 | 2.43 / 2.18 | 16.92 / 16.87 |
| 3 | Cl | H | (furyl) | — | 0 | 0 | $C_{10}H_5N_3OCl_2$ | 116–117 | 47.27 / 47.08 | 1.98 / 1.80 | 16.54 / 16.68 |
| 4 | Cl | H | (thienyl) | — | 0 | 1 | $C_{11}H_7N_3Cl_2S$ | 86–87 | 46.49 / 46.21 | 2.48 / 2.30 | 14.79 / 14.92 |
| 5 | Cl | H | (thienyl) | — | 0 | 0 | $C_{10}H_5N_3Cl_2S$ | 146–147 | 44.46 / 44.25 | 1.87 / 1.68 | 15.56 / 15.68 |
| 6 | Cl | H | (bromothienyl) | — | 0 | 0 | $C_{10}H_4N_3Cl_2SBr$ | 164–165 | 34.41 / 34.67 | 1.16 / 1.03 | 12.04 / 12.09 |
| 7 | Cl | H | (chlorothienyl) | — | 0 | 0 | $C_{10}H_4N_3Cl_3S$ | 166–167 | 39.43 / 39.29 | 1.32 / 1.16 | 13.80 / 13.99 |

-continued

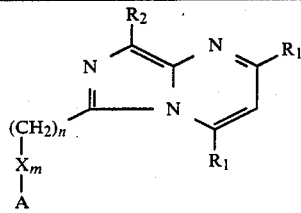

| Example | R₁ | R₂ | A | X | m | n | Formula | mp (°C.) | Analysis Calcd. (%) Found C | H | N |
|---|---|---|---|---|---|---|---|---|---|---|---|
| 8 | Cl | H | (2,5-dimethylthiophene) | — | 0 | 0 | $C_{11}H_7N_3Cl_2S$ | 117–118 | 46.49 / 46.39 | 2.48 / 2.36 | 14.79 / 15.00 |
| 9 | Cl | H | (pyridine) | — | 0 | 0 | $C_{11}H_6N_4Cl_2$ | 140–142 (dec.) | 49.84 / 49.81 | 2.28 / 2.11 | 21.13 / 21.32 |
| 10 | Cl | H | (3-chloro-2-methylbenzothiophene) | — | 0 | 0 | $C_{14}H_6N_3Cl_3S$ | 173–175 | 47.42 / 47.41 | 1.71 / 1.53 | 11.85 / 12.00 |
| 11 | Cl | H | (phenyl) | S | 1 | 1 | $C_{13}H_9N_3Cl_2S$ | 111–112 | 50.34 / 50.41 | 2.92 / 2.79 | 13.55 / 13.60 |
| 12 | Cl | H | (phenyl) | S=O | 1 | 1 | $C_{13}H_9N_3Cl_2SO$ | 153–154 | 47.87 / 47.89 | 2.78 / 2.69 | 12.88 / 12.80 |

EXAMPLE 13

2,4,8-trichloro-6-phenylimidazo[1,5-a]pyrimidine

A mixture of 2,4-dichloro-6-phenylimidazo[1,5-a]pyrimidine (0.88 g), N-chlorosuccinimide (0.5 g) and benzoyl peroxide (0.04 g) in carbon tetrachloride (20 ml) was heated to reflux for 14 hours. The mixture was concentrated and purified by alumina column chromatography, eluting with benzene to give the objective product which was recrystallized from ethanol to yellow plates (0.32 g), mp 133°–134° C.

Analysis (%) for $C_{12}H_6N_3Cl_3$, Calcd. (Found): C, 48.28 (48.36); H, 2.03 (1.81); N, 14.07 (14.35).

Other compounds prepared by the same manner as this example are as follows.

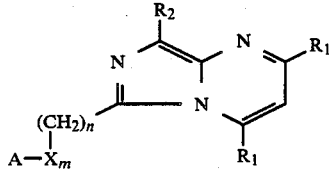

| Example | R₁ | R₂ | A | X | m | n | Formula | mp (°C.) | Analysis Calcd. (%) Found C | H | N |
|---|---|---|---|---|---|---|---|---|---|---|---|
| 14 | Cl | I | (4-methylphenyl) | — | 0 | 0 | $C_{13}H_8N_3Cl_2I$ | 192–193 | 38.65 / 38.65 | 2.00 / 1.90 | 10.40 / 10.39 |
| 15 | Cl | Br | (4-methylphenyl) | — | 0 | 0 | $C_{13}H_8N_3BrCl_2$ | 194–195 | 43.73 / 43.49 | 2.26 / 2.13 | 11.77 / 11.27 |

-continued

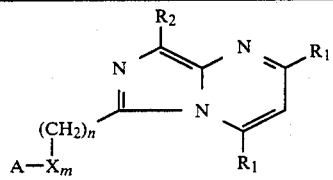

| Example | R₁ | R₂ | A | X | m | n | Formula | mp (°C.) | C | H | N |
|---|---|---|---|---|---|---|---|---|---|---|---|
| 16 | Cl | Cl | 2,4-dichlorophenyl | — | 0 | 0 | $C_{12}H_4N_3Cl_5$ | 186–187 | 39.23 / 39.29 | 1.10 / 0.93 | 11.44 / 11.57 |
| 17 | Cl | Cl | 4-bromophenyl | — | 0 | 0 | $C_{12}H_5N_3BrCl_3$ | 182–183 | 38.19 / 38.25 | 1.34 / 1.12 | 11.13 / 11.15 |
| 18 | Cl | Cl | 4-chlorophenyl | — | 0 | 1 | $C_{13}H_7N_3Cl_4$ | 116–117 | 44.99 / 45.12 | 2.03 / 1.90 | 12.01 / 12.03 |
| 19 | Cl | Cl | cyclohexyl | — | 0 | 0 | $C_{12}H_{12}N_3Cl_3$ | 153–154 | 47.32 / 47.32 | 3.97 / 3.82 | 13.79 / 13.94 |

EXPERIMENT 1

Antifungal spectra

The antifungal activity of the compound of the present invention was assayed by the standard agar dilution streak method against fungi. The results were shown in Table 1. M.I.C. studied with representative members of the compound of this invention have demonstrated extremely favorable antimycotic activity, so that these compounds will be very useful as therapeutic for agents, drugs for animals, fishes and shellfish, and an antiseptic for food.

EXPERIMENT 2

In vivo antifungal activity against systemic infection in mice (ICR)

Mice were infected intraperitoneal with *Candida albicans*. (Strain KYF-1385, challenge dose 2.6–7.2×10⁶ cfu/mouse, n=5). After the infection, compounds were administered 100 mg/kg/day twice a day during 4 days, oral administration.

The efficacy of the compounds of the invention is shown in the Figure together with a control (no treatment).

The present compounds were more effective than the control.

C. albicans KYF-1385

Antifungal activity

Minimum inhibitory concentration (μg/ml)

| Organism | Exp. 1 | Exp. 3 | Exp. 4 | Exp. 5 | Exp. 6 | Exp. 7 | Exp. 8 | Exp. 13 | Exp. 17 | Exp. 18 | Exp. 19 |
|---|---|---|---|---|---|---|---|---|---|---|---|
| *Candida albicans* 3147 | 3.13 | 3.13 | 3.13 | 3.13 | 0.78 | 0.20 | 1.56 | 3.13 | 1.56 | 1.56 | 0.78 |
| *Candida albicans* IFO-1388 | 1.56 | 3.13 | 6.25 | 6.25 | 0.78 | 0.78 | 6.25 | 3.13 | 0.78 | 0.20 | 0.20 |
| *Candida albicans* IFO-1594 | 1.56 | 3.13 | 3.13 | 3.13 | 3.13 | 0.20 | 6.25 | 3.13 | 1.56 | 3.13 | 1.56 |
| *Candida albicans* MTU-12124 | 6.25 | 6.25 | 6.25 | 6.25 | 0.78 | 1.56 | 6.25 | 12.5 | 3.13 | 6.25 | 1.56 |
| *Candida albicans* KYF-602 | 6.25 | 12.5 | 6.25 | 12.5 | 3.13 | 0.39 | 6.25 | 3.13 | 6.25 | 25 | 1.56 |
| *Candida stellatidea* IFO-1398 | 1.56 | 3.13 | 3.13 | 6.25 | 0.78 | 0.78 | 1.56 | 6.25 | 0.39 | 0.78 | 1.56 |
| *Microsporum canis* 200100 | 1.56 | 1.56 | 1.56 | 1.56 | 0.78 | — | — | 0.78 | — | — | — |
| *Aspergillus fumigatus* MTU-06002 | 6.25 | 12.5 | 12.5 | 3.13 | 3.13 | — | — | 6.25 | — | — | — |
| *Trichophyton mentagrophytes* MTU-19003 | 1.56 | 3.13 | 1.56 | 1.56 | 1.56 | 0.78 | 1.56 | 0.78 | 3.13 | 3.13 | 3.13 |
| *Trichophyton mentagrophytes* MTU-19005 | 1.56 | 3.13 | 1.56 | 0.78 | 0.78 | 0.78 | 1.56 | 0.78 | 3.13 | 1.56 | 1.56 |

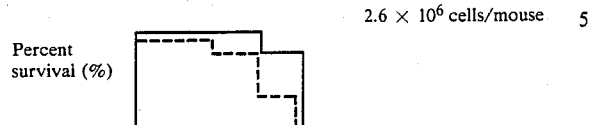

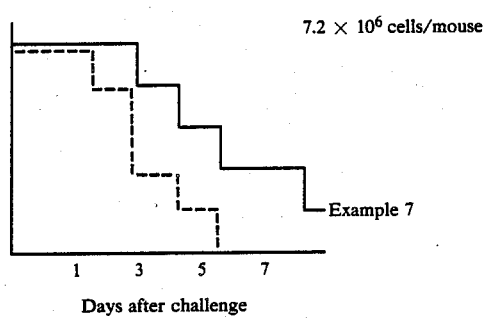

Days after challenge

Effect of present compounds on urine systemic candidosis by oral administration

What we claim is:

1. A compound selected from the group consisting of a free base and its acid addition salts, said free base having the formula (I),

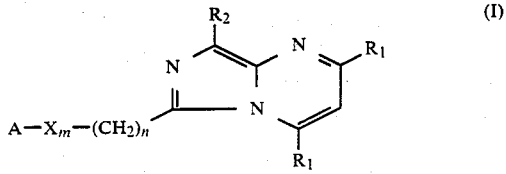

wherein $R_1$ is a halogen atom, $R_2$ is a hydrogen atom or a halogen atom, X is a sulfur atom, a sufinyl group, a sulfonyl group or an oxygen atom, m and n are each independently 0 or 1, A is a phenyl group which may be substituted by 1 or 2 substituents selected from the group consisting of methyl, bromine, and chlorine, a $C_{3-6}$ cycloalkyl group or an aromatic heterocyclic group selected from the group consisting of

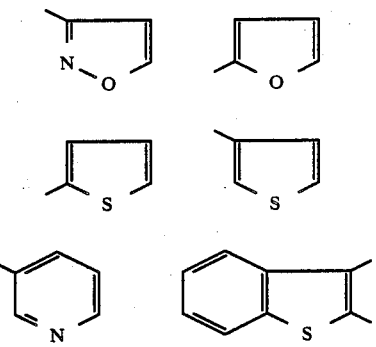

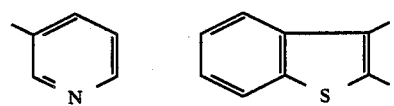

which may be substituted by 1 phenyl, bromine, chlorine, or methyl; with the proviso that when m is 0 and A is a phenyl group which may be substituted or a cycloalkyl group, $R_2$ is not a hydrogen atom.

2. An agent for treatment of fungal diseases comprising a compound as claimed in claim 1 and a pharmaceutically acceptable carrier.

* * * * *